(12) United States Patent
Bin Jamaludin et al.

(10) Patent No.: US 9,057,660 B2
(45) Date of Patent: Jun. 16, 2015

(54) AUTOMATED MULTI-ORIENTATION SHORT DROP TEST APPARATUSES AND METHODS

(75) Inventors: Abd. Halim Bin Jamaludin, Kamunting Perak (MY); Avelino Buenafe, III, Penang (PH)

(73) Assignee: Flextronics Automotive Inc., Newmarket, Ontario (CA)

( * ) Notice: Subject to any disclaimer, the term of this patent is extended or adjusted under 35 U.S.C. 154(b) by 604 days.

(21) Appl. No.: 13/302,410

(22) Filed: Nov. 22, 2011

(65) Prior Publication Data
US 2013/0125616 A1    May 23, 2013

(51) Int. Cl.
*G01M 7/00* (2006.01)
*G01N 3/303* (2006.01)
*G01M 7/08* (2006.01)

(52) U.S. Cl.
CPC *G01M 7/08* (2013.01); *G01N 3/303* (2013.01)

(58) Field of Classification Search
CPC .................................. G01N 3/30; G01N 3/303
USPC ......... 73/12.01, 12.04, 12.06; 901/31, 36, 37, 901/39, 45
See application file for complete search history.

(56) References Cited

U.S. PATENT DOCUMENTS

| | | | | |
|---|---|---|---|---|
| 3,103,116 A | * | 9/1963 | Kohli | 73/12.06 |
| 6,508,103 B1 | * | 1/2003 | Shim et al. | 73/12.06 |
| 6,807,841 B1 | * | 10/2004 | Chen et al. | 73/12.06 |
| 2004/0261493 A1 | * | 12/2004 | Lee | 73/12.09 |
| 2009/0031783 A1 | * | 2/2009 | Fukushima et al. | 73/12.06 |

FOREIGN PATENT DOCUMENTS

JP    2000055778 A  *  2/2000  ............. G01M 7/08

OTHER PUBLICATIONS

Author: Machine translation, Title JP 2000055778 A, Date: Feb. 25, 2000, Publisher: ProQuest on Apr. 15, 2014, pp. 24.*

* cited by examiner

*Primary Examiner* — Harshad R Patel
(74) *Attorney, Agent, or Firm* — Volpe and Koenig, P.C.

(57) ABSTRACT

An Automated Multi-Orientation Drop Test apparatus includes a clamping mechanism for clamping an object to be test dropped. The Automated Multi-Orientation Drop Test apparatus includes a pneumatic lifting mechanism interconnected to the clamping mechanism. The Automated Multi-Orientation Drop Test apparatus includes a guide plate for guiding the object in freefall in a certain orientation such that the object impacts a base in the desired axial orientation.

12 Claims, 5 Drawing Sheets

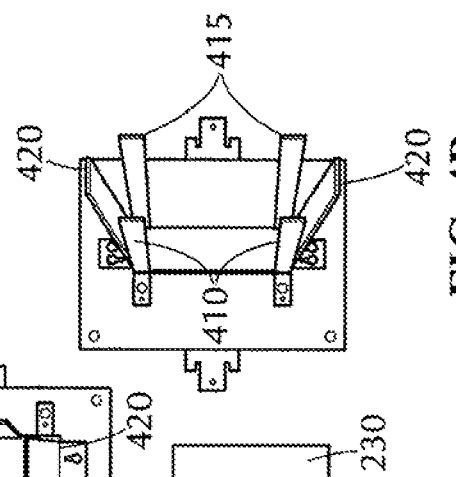
FIG. 4D
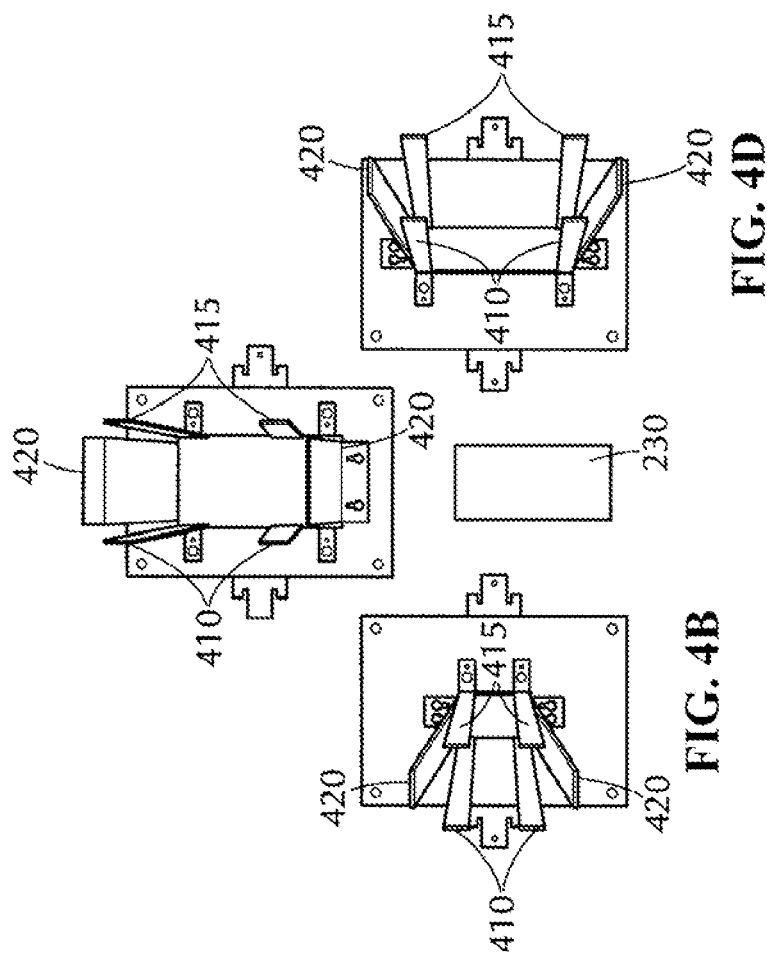
FIG. 4C
FIG. 4B
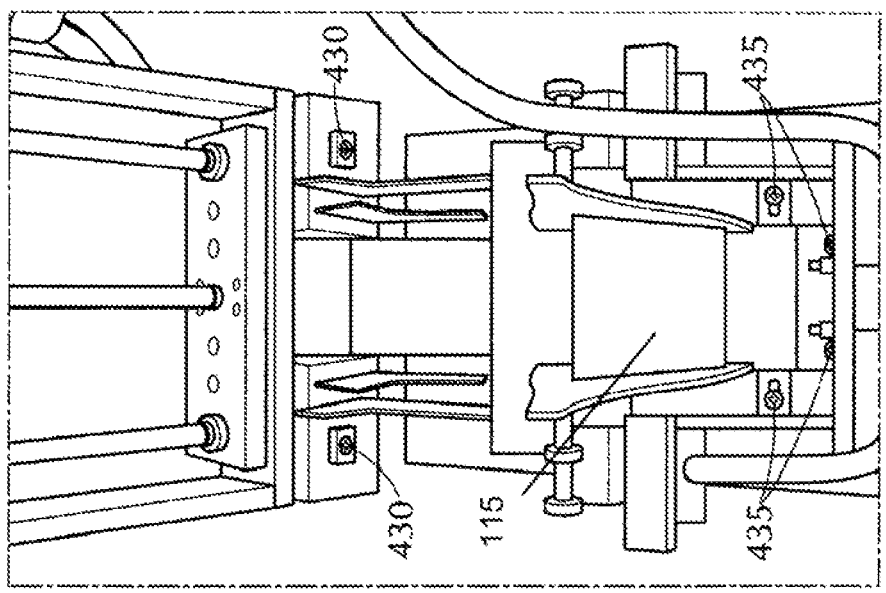
FIG. 4A

AUTOMATED MULTI-ORIENTATION SHORT DROP TEST APPARATUSES AND METHODS

BACKGROUND

Drop testing is an important part of establishing the durability of various electronic devices, components, and other items. Electronic devices may be repeatedly dropped by users and in order to ensure reliability for consumers drop testing is an important part of the qualification process for many products. Additionally, components used in vehicles may be dropped during fabrication and may need to have certain durability characteristics for reliability. Repeated drop tests may be performed by individuals, however, the repeatability of such tests and user error is common leading to inconsistent results. Speed and reliability of the drop angle and position are required. Therefore, a more reliable automated system is needed.

BRIEF SUMMARY

In one embodiment, an Automated Multi-Orientation Drop Test apparatus includes a clamping mechanism for clamping an object to be test dropped. The Automated Multi-Orientation Drop Test apparatus includes a pneumatic lifting mechanism interconnected to the clamping mechanism. The Automated Multi-Orientation Drop Test apparatus includes a guide plate for guiding the object in freefall in a certain orientation such that the object impacts a base in the desired axial orientation. Optionally, the clamping mechanism has first and second arms that are pressed into the object to hold it. In one configuration, the first and second arm of the clamping mechanism each include a bent slot, the bent slot having an approximately wedge shape, each bent slot configured to engage the object. Optionally, the clamping mechanism is configured to hold the object in three configurations, a first configuration configured to hold the object in an x-axis orientation, the first and second arms holding object in a bent slot in each of the first and second arms, the bent slot having an approximately wedge shape, and the second configuration configured to hold the object in a y-axis orientation, the first and second arms holding the object along a longitudinal portion of the arms, terminating in an angled portion of each arm, a third configuration configured to hold the object in a z-axis orientation, the first and second arms holding the object along the longitudinal portion of the arms. In one alternative, the guide plate includes a mechanism for configuring the guide plate in a first, second, and third guide plate configuration, corresponding to the first, second and third configurations of the clamping mechanism. Optionally, the pneumatic lifting mechanism includes a release mechanism that releases the clamping mechanism and the object into a freefall. In one alternative, the Automated Multi-Orientation Drop Test apparatus includes a sensing mechanism that detects when the clamping mechanism and the object are touching the base and activates the pneumatic lifting mechanism to lift the clamping mechanism and the object to a maximum height. In another alternative, the Automated Multi-Orientation Drop Test apparatus includes a maximum height adjustment mechanism, the maximum height adjustment mechanism preventing the pneumatic mechanism from raising the clamping mechanism and the object to the maximum height, instead raising it to a secondary height. Optionally, the maximum height adjustment mechanism is a bumper. Optionally, the pneumatic lifting mechanism is configured to repeatedly release and lift the object and the clamping mechanism, and the lifting and releasing occurs periodically and regularly. Alternatively, the Automated Multi-Orientation Drop Test apparatus includes an interconnection mechanism for connecting with a computer, the interconnection mechanism providing for the control of the pneumatic lifting mechanism. Optionally, the guide plate includes a plurality of guides, the plurality of guides including a first and second front guide, a third and fourth rear guide, and a fifth and sixth side guide, wherein the plurality of guides are oriented to provide an approximately rectangular frame that extends vertically and is configured to fit around the first and second clamping arms during free fall.

In one embodiment, a method of drop testing an object includes providing an Automated Multi-Orientation Drop Test apparatus. The method further includes, adjusting a clamping mechanism of the Automated Multi-Orientation Drop Test apparatus to clamp the object in a first axial configuration. The method in addition includes, adjusting a guide plate of the Automated Multi-Orientation Drop Test to correspond to the first axial configuration. Moreover, the method includes, activating the Automated Multi-Orientation Drop Test apparatus for a set period of time to perform a drop test, wherein the Automated Multi-Orientation Drop Test apparatus repeatedly drops and raising the object using a pneumatic lifting mechanism periodically, such that a number of drops occur within the set period of time. Optionally, the method includes adjusting the clamping mechanism of the Automated Multi-Orientation Drop Test apparatus to clamp the object in a second axial configuration; adjusting the guide plate of the Automated Multi-Orientation Drop Test to correspond to the second axial configuration; and activating the Automated Multi-Orientation Drop Test apparatus for the set period of time to perform the drop test, wherein the Automated Multi-Orientation Drop Test apparatus repeatedly drops and raising the object using the pneumatic lifting mechanism periodically, such that the number of drops occur within the set period of time. Optionally, the method includes adjusting the clamping mechanism of the Automated Multi-Orientation Drop Test apparatus to clamp the object in a third axial configuration; adjusting the guide plate of the Automated Multi-Orientation Drop Test to correspond to the third axial configuration; and activating the Automated Multi-Orientation Drop Test apparatus for the set period of time to perform the drop test, wherein the Automated Multi-Orientation Drop Test apparatus repeatedly drops and raising the object using the pneumatic lifting mechanism periodically, such that the number of drops occur within the set period of time. In one alternative, the first, second, and third axial configuration correspond with an x, y, and z axis of the object, wherein the x, y, and z axis are the standard three dimensional axes.

BRIEF DESCRIPTION OF THE DRAWINGS

FIG. 4a-d shows three configurations of one embodiment of a guide plate for use with the AMODT of FIG. 1.

DETAILED DESCRIPTION

Figure 1:
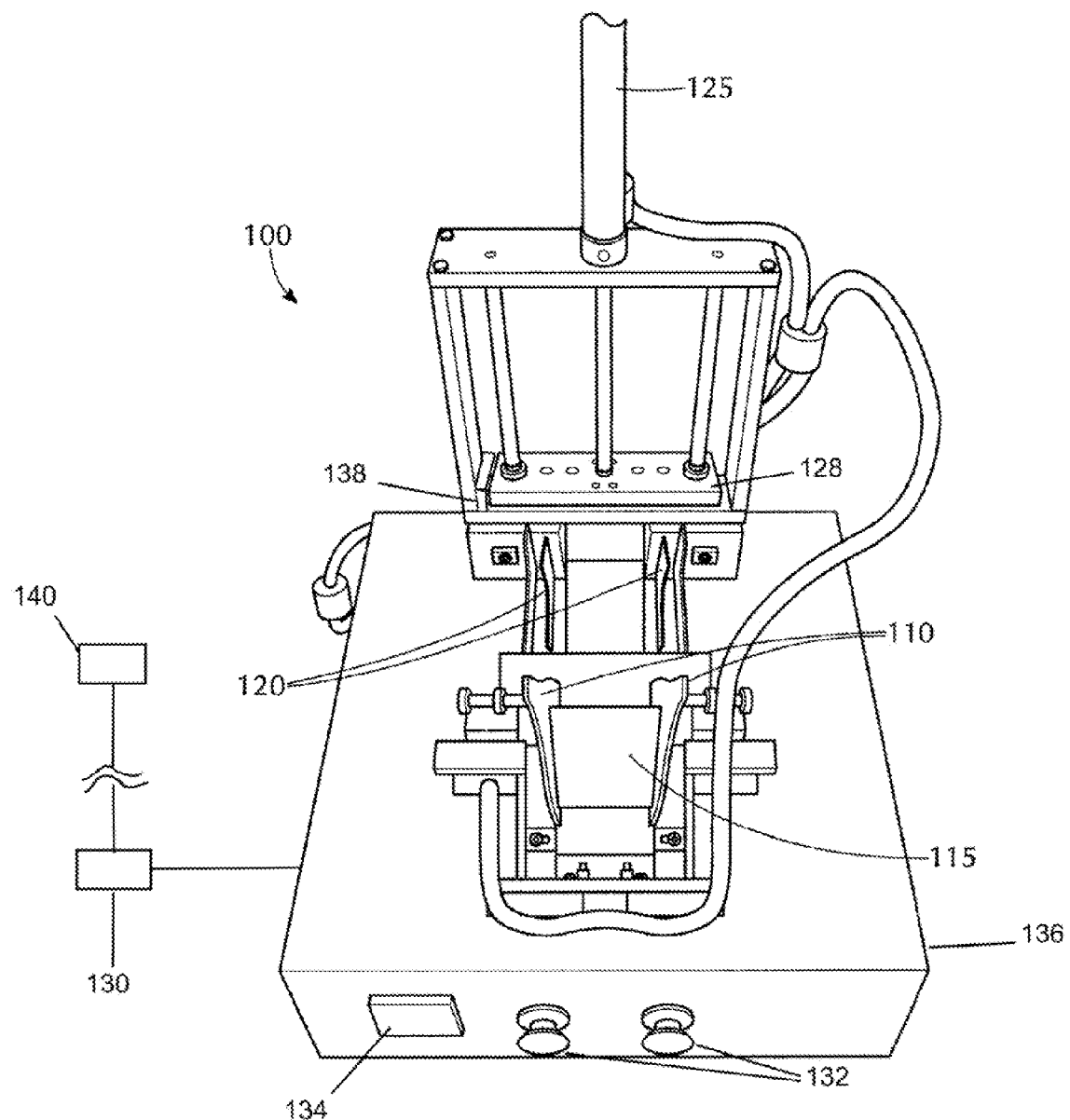
FIG. 1 shows one embodiment of an Automated Multi-Orientation Drop Test (AMODT) apparatus and method.

Certain terminology is used herein for convenience only and is not to be taken as a limitation on the embodiments of a capacitor sensor for Automated Multi-Orientation Drop Test (AMODT) apparatus. In the drawings, the same reference letters are employed for designating the same elements throughout the several figures.

The words "right", "left", "front", and "back" designate directions in the drawings to which reference is made. The words "inwardly" and "outwardly" refer to directions toward and away from, respectively, the geometric center of the AMODT and designated parts thereof. The terminology includes the words above specifically mentioned, derivatives thereof, and words of similar import.

Like reference numerals designate like or corresponding parts throughout the various views and with particular reference to each of Figures as delineated below.

FIG. 1 shows one embodiment of an Automated Multi-Orientation Drop Test (AMODT) apparatus and method. AMODT is convertible for testing from various distances. In the embodiment shown in FIG. 1, AMODT is convertible from a distance of 10 cm to 15 cm for a short drop test. Other configurations are possible including various shorter and greater drop distances including but not limited distances from 1 cm to several meters. The AMODT has easily convertible drop fixtures so that a variety of objects may be tested. The axis that the object is dropped along may be converted for impact of the object on any one of three axes. Using these machines the drops per minute may be greatly increased.

The basic configuration of the AMODT 100 can be seen in FIG. 1, including the activation buttons 132 and drop counter 134 of the face of the device. Various embodiments may have different systems for activating and counting as explained below. The AMODT 100 also includes a solid base area 136 for absorbing the impact of drop testing.

Figure 2A:
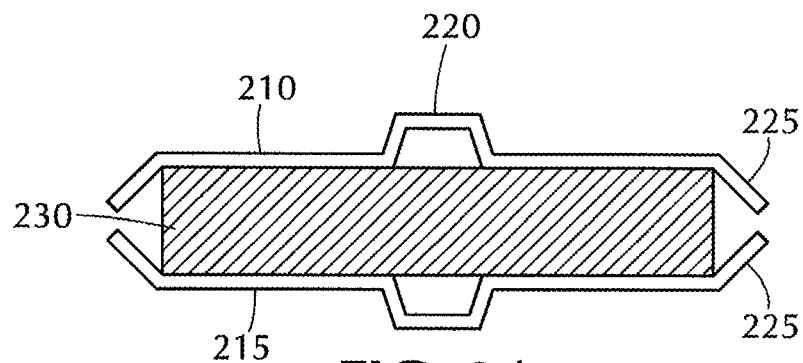
FIG. 2A shows an embodiment of damper mechanisms according for use with the AMODT of FIG. 1 holding an object in a first orientation.
Figure 2B:
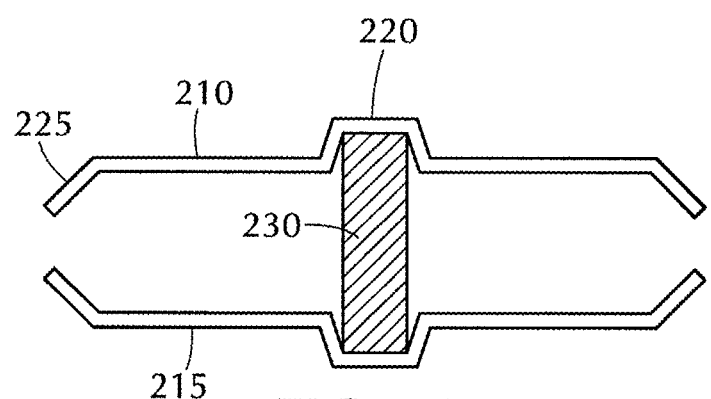
FIG. 2B shows an embodiment of damper mechanisms according for use with the AMODT of FIG. 1 holding an object in a second orientation.
Figure 2C:
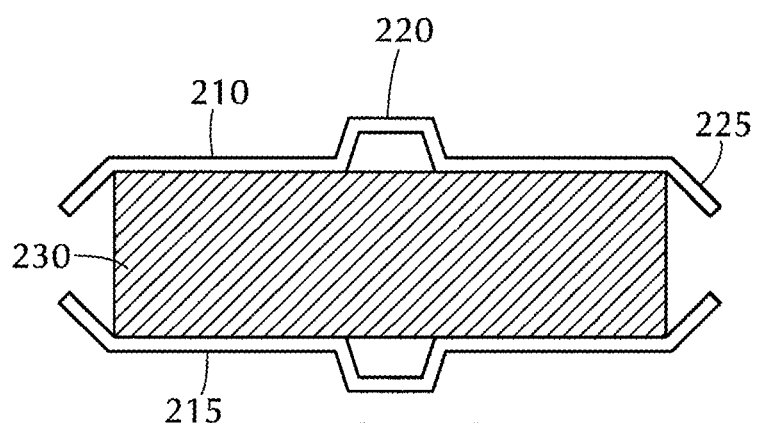
FIG. 2C shows an embodiment of damper mechanisms according for use with the AMODT of FIG. 1 holding an object in a third orientation.

As can be seen in FIG. 1, AMODT 100 includes a fixture clamper 110. Fixture clamper 110 is configured to fit around and clamp the object to be dropped. The current configuration is configured to clamp to an approximately rectangular box type object. Additional views of clamper 110 are shown in FIGS. 2a-d. Clamper 110 includes a first and second arm, 210, 215. First and second arm 210, 215 each include a first bent slot 220 and angle ends 225. The configuration of the first and second arm 210, 215 provide for holding of the rectangular object 230 in the three axis positions. FIG. 2b shows the rectangular object 230 in a first configuration with the object 230 in the first bent slot 220. First and second arm 210, 215 apply pressure to the object 230 and the v shaped nature of first bent slot firmly holds the rectangular object in place. FIG. 2c shows a second configuration of object 230. Similarly, first and second arm 210, 215 apply pressure to rectangular object 230 and hold in place between angled ends 225. The three configurations of drop testing are used to determine the durability of the object at multiple drop positions.

Referring back to FIG. 1, the AMODT 100 includes a guide plate 115 for guiding the fall of object 230 (FIGS. 2a-c) during drop testing. The clamper mechanism 120 provides for the clamper 110 to clamp to accommodate the various sizes and positions of object 230 (FIGS. 2a-c). AMODT also includes Pneumatic Cylinder 125. Pneumatic Cylinder 125 is attached to clamper 110 and provides for the dropping and raising of object 230 (FIGS. 2a-c). During dropping operations pneumatic cylinder 125 releases and object 230 (FIGS. 2a-c) free falls and impacts in it configured orientation guided by guide plate 115.

Figure 3:
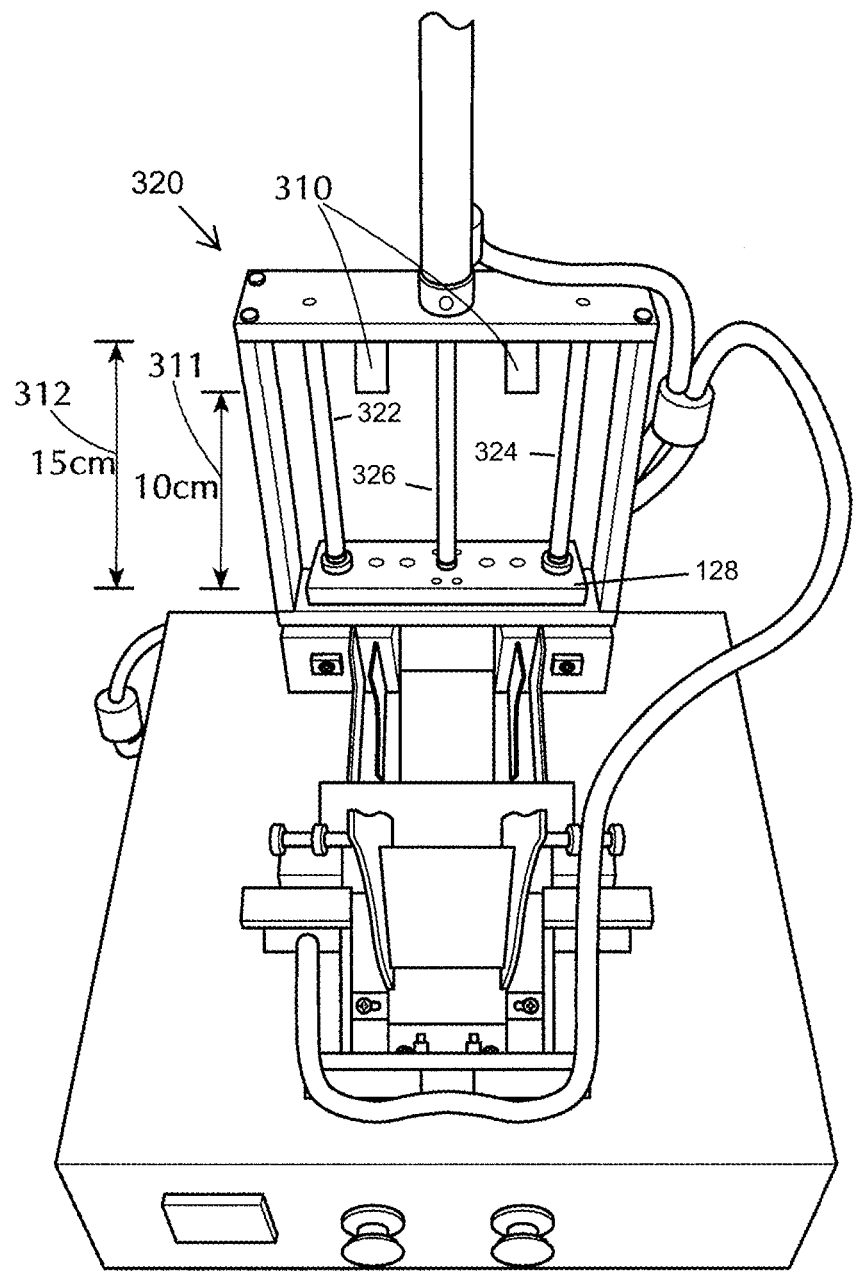
FIG. 3 shows an embodiment of the AMODT apparatus of FIG. 1.

As shown in FIG. 3, various sized stops may be installed to adjust the drop height. As shown, stops 310 provide for conversion from a drop height of 15 cm to a drop height of 10 cm. The drop testing mechanism 320, is mounted on vertical tubes 322, 324, 326 that provide for uniform drop characteristic between drops. The drop plate 128 falls along the outer tubes 322, 324 when the drop is released and is raised using the mechanically actuated center tube 326. The mechanism for actuating the tube may be motor driven with an electric motor or hydraulic or otherwise actuated.

FIG. 4a-d shows three configurations of the guide plate 115. These three configurations accommodate the three axial configurations of the object 230. Each guide plate 115 includes 6 guides, front guides 410, rear guides 415, and side guides 420. As shown in FIG. 4a damper adjustment mechanism 430 and guide plate adjustment mechanism 435 provides the configurations of the guide plate 115. FIG. 4b shows a first configuration. This configuration provides for a z axis drop. FIG. 4c provides a second configuration. This is for x-axis drops. FIG. 4d provides for a third configuration allowing for y-axis drops. In operation the operator configures the axis orientation desired. The object 230 is loaded. The device may be programmed to perform a set number of drops by including a microcontroller or by providing for connection to a computer running programs such as LabView or other testing software. Alternatively, since the speed of drop and the operation of the pneumatic mechanism is know, a set number of drops will occur during a time period, so the device may be merely turned on and off on set intervals.

In one embodiment the AMODT 100 includes an interconnection mechanism 130 for a computer system 140. The computer system 140 may execute LabView or other control software. A test count sensor 138 may be included to count the number of drop an object incurs during testing. The sensor 138 may be a proximity sensor such a photoreceptor that is covered as the drop plate 128 descends. Other types of proximity sensors will occur to those skilled in the art in light of this disclosure, including non-contact sensors including magnetic fields, light and other indication methodologies. The sensor 138 may also be used to indicate to the system that the device should be actuated to lift and drop the object again. The computer system 140 including software may collected statistics on drops. The system may even include an accelerometer in the AMODT. The accelerometer may be read by the computer and software to measure and ensure proper performance of the system, ensuring that each drop is reflective of free fall acceleration. Statistics on accelerometer readings may also be collected by the computer system 140 that is interconnected to AMODT 100.

Figure 5:
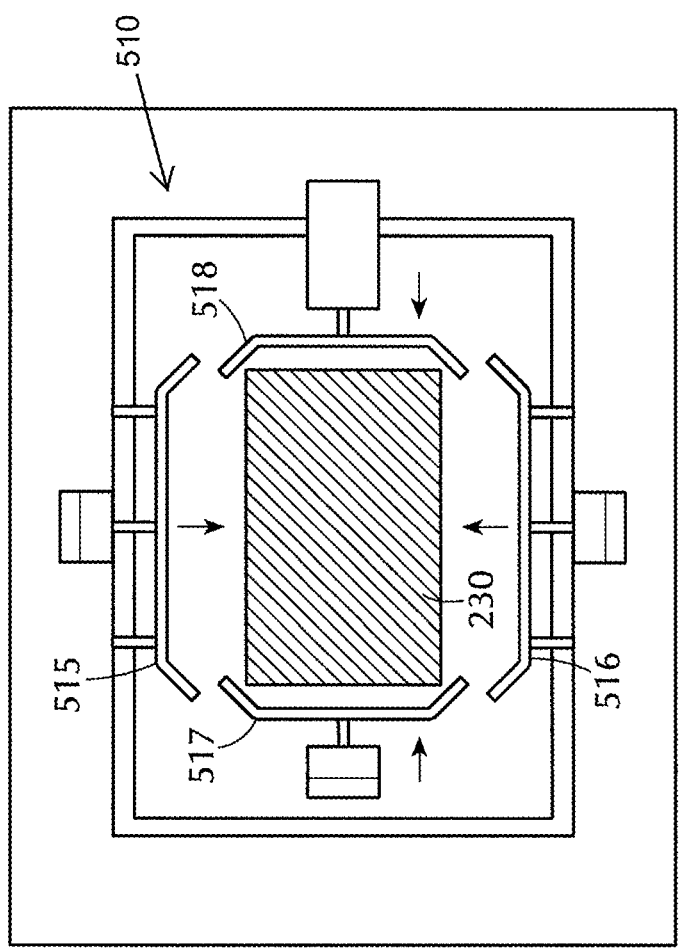
FIG. 5 shows an alternative embodiment of a damper mechanism.

In FIG. 5 an alternative embodiment of a damper 110 is shown. Clamper 510 includes four damper arms 515-518. These damper arms 515-518 may be advanced to the object and oriented to hold it in place. In any case the damper arms should be less than any thickness of the object tested, or in the alternative the object will have to be carefully oriented in the clamps so it extends beyond the clamps and sustains the impact.

The embodiments described above and shown herein are illustrative and not restrictive. The scope of the Automated Multi-Orientation Drop Test apparatus and associated systems and methods is indicated by the claims rather than by the foregoing description and attached drawings. The Automated Multi-Orientation Drop Test apparatus may be embodied in other specific forms without departing from the spirit of the Automated Multi-Orientation Drop Test apparatus. Accordingly, these and any other changes which come within the scope of the claims are intended to be embraced therein.

The invention claimed is:

1. An Automated Multi-Orientation Drop Test apparatus comprising:
   a) a clamping mechanism for clamping an object to be test dropped, the clamping mechanism having first and second arms that are pressed into the object to hold the object;
   b) a pneumatic lifting mechanism interconnected to the clamping mechanism;
   c) a guide plate for guiding the object in freefall in a certain orientation such that the object impacts a base in the desired axial orientation,
   wherein the clamping mechanism is configured to hold the object in three configurations, a first configuration configured to hold the object in an x-axis orientation, the first and second arms holding object in a bent slot in each of the first and second arms, the bent slot having an approximately wedge shape, and configuration configured to hold the object in a y-axis orientation, the first and second arms holding the object along a longitudinal portion of the arms, terminating a an angled portion of each arm, a third configuration configured to hold the object in a z-axis orientation, the first and second arms holding the object along the longitudinal portion of the arms,
   wherein the guide plate includes a mechanism for configuring the guide plate in a first, second, and third guide plate configuration, corresponding to the first, second and third configurations of the clamping mechanism, and
   wherein the guide plate includes a plurality of guides, including a first and second front guide, a third and fourth rear guide, and a fifth and sixth side guide, wherein the plurality of guides are oriented to provide an approximately rectangular frame that extends vertically during free fall.

2. The Automated Multi-Orientation Drop Test apparatus of claim 1, wherein the first and second arm of the clamping mechanism each include a bent slot, the bent slot having an approximately wedge shape, each bent slot configured to engage the object.

3. The Automated Multi-Orientation Drop Test apparatus of claim 1, wherein the pneumatic lifting mechanism includes a release mechanism that releases the clamping mechanism and the object into a freefall.

4. The Automated Multi-Orientation Drop Test apparatus of claim 3 further comprising a sensing mechanism that detects when the clamping mechanism and the object are touching the base and activates the pneumatic lifting mechanism to lift the clamping mechanism and the object to a maximum height.

5. The Automated Multi-Orientation Drop Test apparatus of claim 4, further comprising a maximum height adjustment mechanism, the maximum height adjustment mechanism preventing the pneumatic mechanism from raising the clamping mechanism and the object to the maximum height, instead raising it to a secondary height.

6. The Automated Multi-Orientation Drop Test apparatus of claim 5, wherein the maximum height adjustment mechanism is a bumper.

7. The Automated Multi-Orientation Drop Test apparatus of claim 4, wherein the pneumatic lifting mechanism is configured to repeatedly release and lift the object and the clamping mechanism, and the lifting and releasing occurs periodically and regularly.

8. The Automated Multi-Orientation Drop Test apparatus of claim 4, further comprising an interconnection mechanism for connecting with a computer, the interconnection mechanism providing for the control of the pneumatic lifting mechanism.

9. A method of drop testing an object, comprising:
   a) providing the Automated Multi-Orientation Drop Test apparatus of claim 1;
   b) adjusting the clamping mechanism of the Automated Multi-Orientation Drop Test apparatus to clamp the object in a first axial configuration;
   c) adjusting the guide plate of the Automated Multi-Orientation Drop Test to correspond to the first axial configuration such that the object impacts a base in the first axial configuration guided by the guide plate;
   d) activating the Automated Multi-Orientation Drop Test apparatus for a set period of time to perform a drop test, wherein the Automated Multi-Orientation Drop Test apparatus repeatedly drops and raising the object using a pneumatic lifting mechanism periodically, such that a number of drops occur within the set period of time.

10. The method of claim 9, further comprising:
    a) adjusting the clamping mechanism of the Automated Multi-Orientation Drop Test apparatus to clamp the object in a second axial configuration;
    b) adjusting the guide plate of the Automated Multi-Orientation Drop Test to correspond to the second axial configuration;
    c) activating the Automated Multi-Orientation Drop Test apparatus for a set period of time to perform a drop test, wherein the Automated Multi-Orientation Drop Test apparatus repeatedly drops and raising the object using the pneumatic lifting mechanism periodically, such that the number of drops occur within the set period of time.

11. The method of claim 10, further comprising:
    a) adjusting the clamping mechanism of the Automated Multi-Orientation Drop Test apparatus to clamp the object in a third axial configuration;
    b) adjusting the guide plate of the Automated Multi-Orientation Drop Test to correspond to the third axial configuration;
    c) activating the Automated Multi-Orientation Drop Test apparatus for a set period of time to perform a drop test, wherein the Automated Multi-Orientation Drop Test apparatus repeatedly drops and raising the object using the pneumatic lifting mechanism periodically, such that the number of drops occur within the set period of time.

12. The method of claim 11, wherein the first, second, and third axial configuration correspond with an x, y, and z axis of the object, wherein the x, y, and z axis are a standard three dimensional axis.

* * * * *